United States Patent
Halpern et al.

(10) Patent No.: US 8,217,946 B2
(45) Date of Patent: Jul. 10, 2012

(54) GRAPHICAL DISPLAY FOR PHYSIOLOGICAL PATIENT DATA

(75) Inventors: Arieh S. Halpern, Beverly Hills, CA (US); Cary Talbot, Santa Clarita, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 13/228,138

(22) Filed: Sep. 8, 2011

(65) Prior Publication Data

US 2012/0001920 A1 Jan. 5, 2012

Related U.S. Application Data

(63) Continuation of application No. 11/929,979, filed on Oct. 30, 2007, now abandoned.

(51) Int. Cl.
*G06T 11/20* (2006.01)
(52) U.S. Cl. ..................... 345/440; 345/440.2
(58) Field of Classification Search ............. 345/440
See application file for complete search history.

(56) References Cited

U.S. PATENT DOCUMENTS

| | | | | |
|---|---|---|---|---|
| 5,136,690 | A * | 8/1992 | Becker et al. | 715/853 |
| 5,438,983 | A * | 8/1995 | Falcone | 600/301 |
| 5,562,621 | A * | 10/1996 | Claude et al. | 604/100.03 |
| 2005/0203360 | A1 * | 9/2005 | Brauker et al. | 600/345 |
| 2008/0146895 | A1 * | 6/2008 | Olson et al. | 600/301 |

* cited by examiner

*Primary Examiner* — Michelle L Sams
(74) *Attorney, Agent, or Firm* — Ingrassia Fisher & Lorenz, P.C.

(57) ABSTRACT

An intuitive graphical display as described herein can be rendered by a host device that obtains physiological patient data (such as blood glucose values) in real time or substantially real time. The graphical display includes a calibrated bar graph having a desired measurement range for the monitored parameter. The graphical display also includes a dynamic measurement value indicator that moves along the bar graph in a manner that tracks the current value of the monitored physiological characteristic. The graphical display may also incorporate easy-to-interpret display elements that allow the user to quickly determine whether the current value of the monitored physiological characteristic is within or outside a normal range, whether the monitored physiological characteristic is rising or falling, and the approximate rate of change of the monitored physiological characteristic.

11 Claims, 7 Drawing Sheets

GRAPHICAL DISPLAY FOR PHYSIOLOGICAL PATIENT DATA

CROSS-REFERENCE TO RELATED APPLICATION

This application is a continuation of U.S. patent application Ser. No. 11/929,979, filed Oct. 30, 2007.

TECHNICAL FIELD

Embodiments of the subject matter described herein relate generally to devices that monitor one or more conditions of a patient. More particularly, embodiments of the subject matter relate to a graphical user interface that displays physiological patient data on a monitor or other device.

BACKGROUND

The prior art includes devices, systems, and equipment designed to process and display medical data for a patient. For example, patient monitoring equipment is often used to graphically display a patient's heart rate, blood pressure, and other measured physiological characteristics. The prior art also includes medical devices that are intended for personal use by the patient or the patient's caregiver; such medical devices may be designed to be carried by the patient or designed for use in the home. For example, diabetics are usually required to modify and monitor their daily lifestyle to keep their body in balance, in particular, their blood glucose (BG) levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of insulin pump systems that are designed to deliver accurate and measured doses of insulin via infusion sets (an infusion set delivers the insulin through a small diameter tube that terminates at a cannula inserted under the patient's skin). In lieu of a syringe, the patient can simply activate the insulin pump to administer an insulin bolus as needed, for example, in response to the patient's current BG level. A patient can measure his BG level using a BG measurement device, such as a test strip meter, a continuous glucose measurement system, or the like. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement can be displayed on the BG measurement device and/or the BG measurement device can transfer the measurement data to another device, such as a continuous glucose monitoring system that monitors the patient's BG level in substantially real time.

Insulin pumps and continuous glucose monitoring devices may also be configured to communicate with remote control devices, monitoring or display devices, BG meters, and other devices associated with such an infusion system. Any of the individual devices within an infusion system may include a display element, and it is desirable to utilize these display elements to display the patient's BG level. Historically, BG levels have been displayed numerically or as a graph over time. Although such graphical displays might adequately convey the BG level information, they can be limited in the amount of additional information they provide. Moreover, such graphical displays may not be intuitive and easy to read.

BRIEF SUMMARY

A graphical user interface as described here is designed to convey physiological patient data in an intuitive and easy to read format. The graphical user interface is capable of displaying the current value of a monitored physiological characteristic (e.g., BG level), along with additional information related to the monitored physiological characteristic. Various graphical elements and displayed fields of the graphical user interface may have dynamically adjustable display characteristics that respond to the changing value of the monitored physiological parameter. The intuitive graphical display of physiological patient data can be rendered by any compatibly configured electronic device, regardless of form factor. For example, a graphical display of continuous BG data may be rendered on an insulin infusion pump, a remote glucose monitor, a cellular telephone, a personal computer, a personal digital assistant, or the like.

The above and other features may be implemented by an embodiment of an electronic device having rendered thereon an intuitive graphical display of physiological patient data. The graphical display includes: a calibrated bar graph that indicates a measurement range for a monitored physiological characteristic; and a measurement value pointer that moves along the calibrated bar graph to indicate a current value of the monitored physiological characteristic and a direction of change of the monitored physiological characteristic.

The above and other aspects may be carried out by an embodiment of an electronic device having an electronic display, where the electronic device performs a method of providing an intuitive graphical display of physiological patient data. The method involves: obtaining data corresponding to a monitored physiological characteristic; generating, for display on the electronic display, a graphical element comprising a calibrated bar graph that indicates a measurement range for the monitored physiological characteristic, and a measurement value pointer that moves along the calibrated bar graph to indicate a current value of the monitored physiological characteristic and a direction of change of the monitored physiological characteristic; and rendering the graphical element on the electronic display.

The above and other aspects may be carried out by an embodiment of a method for displaying, on an electronic display of a device, an intuitive graphical display of physiological patient data. The method involves: obtaining, at the device, data corresponding to a monitored physiological characteristic; displaying, on the electronic display, a bar graph that indicates a measurement range for the monitored physiological characteristic; and displaying, on the electronic display, a measurement value pointer that indicates a current value of the monitored physiological characteristic on the bar graph, and that indicates a direction of change of the monitored physiological characteristic.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the invention or the application and uses of such embodiments. Furthermore, there is no intention to be bound by any expressed or implied theory presented in the preceding technical field, background, brief summary or the following detailed description.

Techniques and technologies may be described herein in terms of functional and/or logical block components and various processing steps. It should be appreciated that such block components may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments may be practiced in conjunction with any number of display formats and protocols and that the system described herein is merely one suitable example.

For the sake of brevity, conventional techniques related to data transmission, signaling, the generation of electronic displays, computer graphics, infusion system operation, insulin pump and/or infusion set operation, blood glucose sensing and monitoring, and other functional aspects of the systems (and the individual operating components of the systems) may not be described in detail here. Examples of infusion pumps and/or communication options may be of the type described in, but not limited to, U.S. Pat. Nos. 4,562,751; 4,685,903; 5,080,653; 5,505,709; 5,097,122; 6,554,798; 6,558,320; 6,558,351; 6,641,533; 6,659,980; 6,752,787; 6,817,990; and 6,932,584, which are herein incorporated by reference. Examples of glucose sensing and/or monitoring devices may be of the type described in, but not limited to, U.S. Pat. Nos. 6,484,045; 6,809,653; 6,892,085; and 6,895,263, which are herein incorporated by reference. Furthermore, the connecting lines shown in the various figures contained here are intended to represent example functional relationships and/or physical couplings between the various elements. It should be noted that many alternative or additional functional relationships or physical connections may be present in an embodiment of the described subject matter.

The following description may refer to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically.

Figure 1:
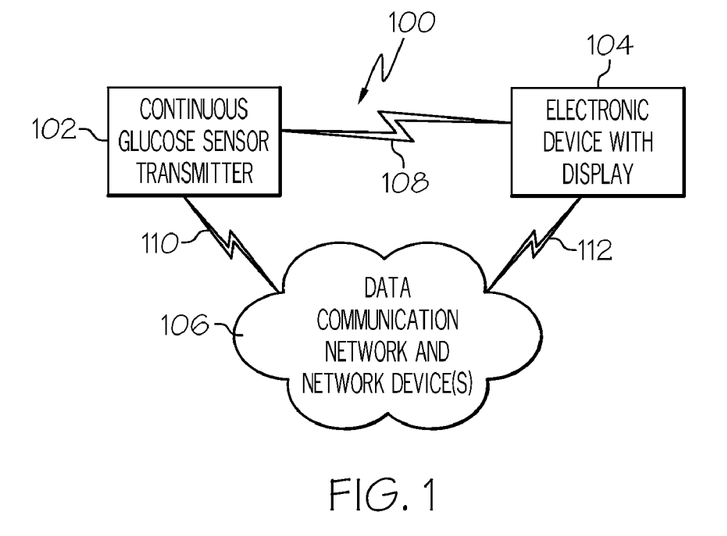
FIG. 1 is a schematic representation of an embodiment of a system for displaying physiological patient data.

FIG. 1 is a schematic representation of an embodiment of a system 100 for displaying physiological patient data, such as BG data. Although the following description refers to the display of BG data, system 100 and the various graphical displays mentioned herein can be suitably configured for use with other types of physiological patient data, including, without limitation: cardiac data; electrolyte data; blood pressure data; or the like.

System 100 is depicted as a simple deployment that includes a continuous glucose sensor transmitter 102 that directly and/or indirectly communicates with an electronic device 104 having an associated electronic display, which may be integral to electronic device 104 or coupled to electronic device 104. System 100 may also include a data communication network and one or more network devices (collectively identified by reference number 106). As depicted in FIG. 1, continuous glucose sensor transmitter 102 may directly communicate with electronic device 104 via a wireless link 108. Alternatively, continuous glucose sensor transmitter 102 may indirectly communicate with electronic device 104 via a wireless link 110, network and network devices 106, and a wireless link 112. It should be appreciated that any of these links may alternatively be realized using wired links. Furthermore, an embodiment of electronic device 104 need not obtain the BG data exclusively from continuous glucose sensor transmitter 102; an embodiment may be suitably configured to obtain the BG data from one or more different devices (or manually) in addition to, or in lieu of, continuous glucose sensor transmitter 102.

As used here, a "data communication network" represents any number of physical, virtual, or logical components, including hardware, software, firmware, and/or processing logic configured to support data communication between an originating component and a destination component, where data communication is carried out in accordance with one or more designated communication protocols over one or more designated communication media. Communication hardware utilized by a data communication network may include a mechanically detachable unit such as an SDIO, a USB ready wireless module, or the like. For example, a data communication network may include, without limitation: a computer network such as a local area network or a wide area network; a pager network; a cellular telecommunication network; a cordless telephone system; an 802.11 network (WiFi); an 802.16 network (WiMAX); the Internet; IEEE P1901 BPL (Broadband over Power Lines); a hospital data communication network (WMTS or other); a home network, such as a home control network, a home security system, or a home alarm system; the public switched telephone network; a satellite communication network; or the like. In practice, data communication between continuous glucose sensor transmitter 102 and electronic device 1104 may be routed by two or more different types of data communication networks using known or proprietary network interfacing techniques.

Continuous glucose sensor transmitter 102 is suitably configured to measure the BG level of a patient (i.e., a physiological characteristic of the patient) in a continuous manner. Sensor transmitter 102 may, for example, include a direct blood contact sensor, a subcutaneous sensor, a noninvasive sensor, and/or other continuous glucose sensing technologies that are currently known or developed in the future. In the exemplary system 100 described here, continuous glucose sensor transmitter 102 measures the BG level of the patient in real time or substantially real time. Continuous glucose sensor transmitter 102 may include a wireless transmitter that facilitates transmission of the BG data to other devices within system 100, in particular electronic device 104. In practice, continuous glucose sensor transmitter 102 can be set up such that it periodically transmits updated BG measurements. For example, continuous glucose sensor transmitter 102 may be suitably configured to transmit a current BG value once every five minutes.

Electronic device 104, which may assume any practical form factor, includes at least one electronic display for rendering intuitive graphical displays as described below. For example, electronic device 104 may be realized as any of the following devices, without limitation: a patient-wearable monitor; a patient-wearable fluid infusion pump; a remote display monitor; a patient monitor, such as a vital signs monitor; a measurement device for the monitored physiological characteristic; a wireless telephone; a computing device; a television; a personal digital assistant; a digital media player; and a portable video game device. In this regard, electronic device 104 may be based upon the glucose sensing and/or monitoring devices described in U.S. Pat. Nos. 6,484,045, 6,809,653, 6,892,085, and 6,895,263. Alternatively or additionally, electronic device 104 may be based upon the various network devices and local infusion system devices described in United States patent application publication number 2007/0255125, titled Monitor Devices for Networked Fluid Infusion Systems, which is incorporated herein by reference. Alternatively or additionally, electronic device 104 may be based upon the monitor device described in United States patent application publication number 2008/0300572, titled Wireless Monitor for a Personal Medical Device System, which is incorporated herein by reference.

Figure 2:
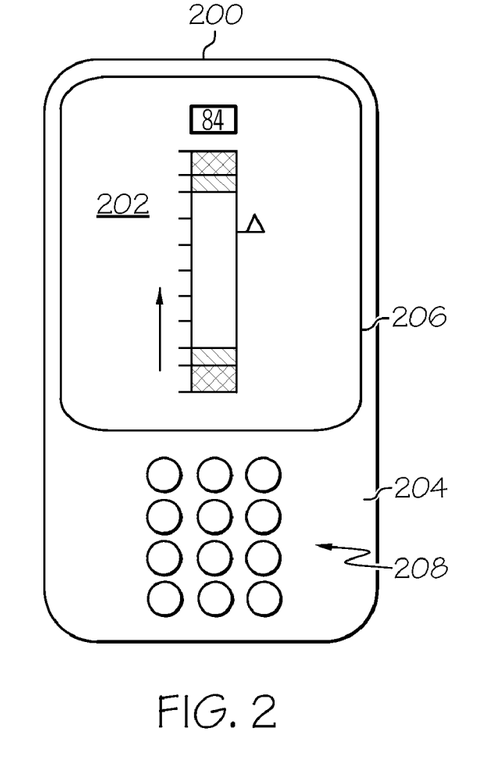
FIG. 2 is a face view of an embodiment of an electronic device having rendered thereon an intuitive graphical display of physiological patient data.
Figure 3:
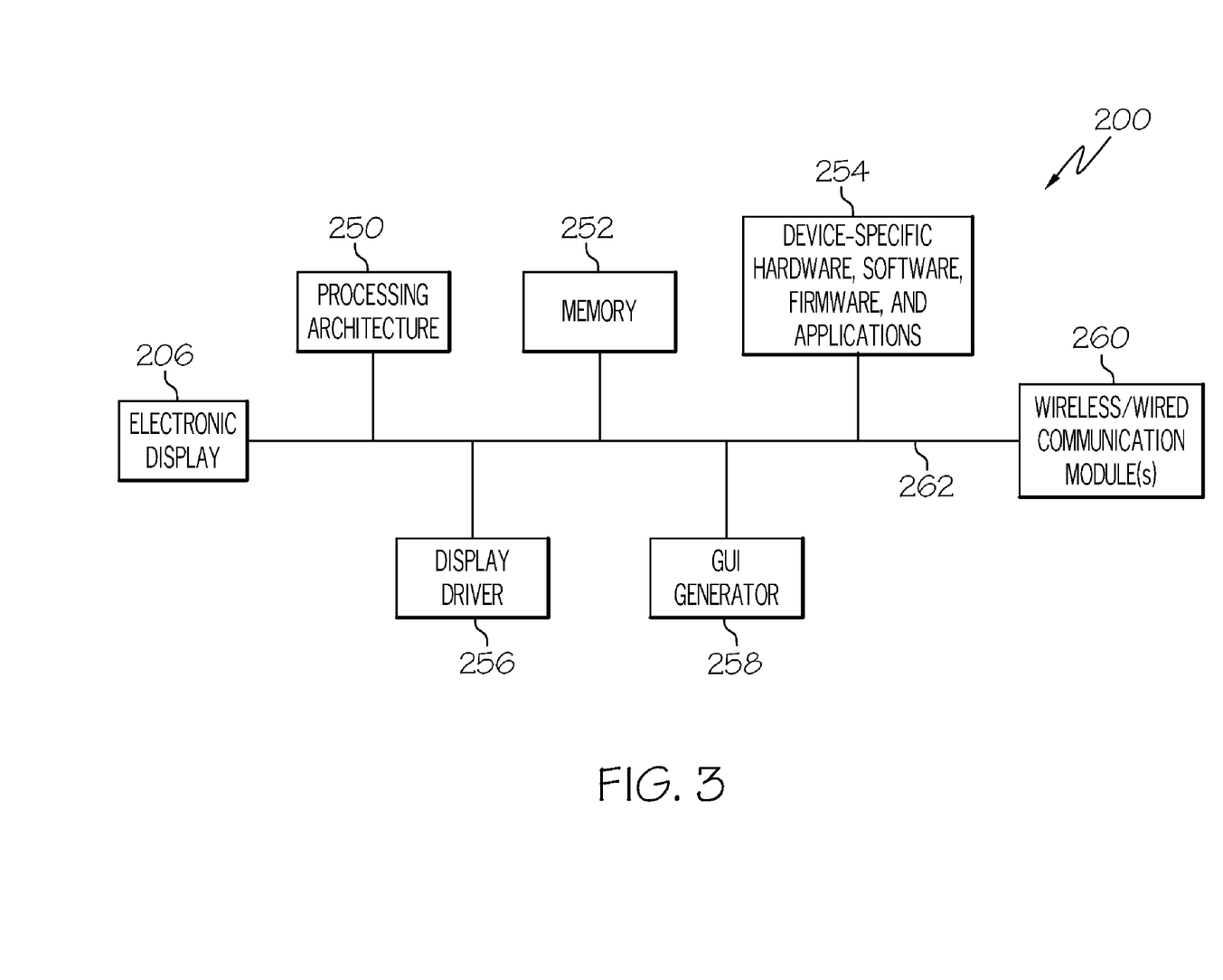
FIG. 3 is a schematic representation of an embodiment of an electronic device that is configured to generate an intuitive graphical display of physiological patient data.

FIG. 2 is a face view of an embodiment of an electronic device 200 having rendered thereon an intuitive graphical display 202 of physiological patient data, and FIG. 3 is a schematic representation of an embodiment of electronic device 200. The general architecture depicted in FIG. 3 may of course apply to other electronic devices having a different form factor than that shown in FIG. 2. Electronic device 200 is depicted as a portable instrument (such as a smart phone or a personal digital assistant) in FIG. 2. Electronic device 200 generally includes, without limitation: a housing 204; an electronic display 206; and a keypad 208. Although not shown in FIG. 2, electronic device 200 may include a number of conventional and well known features, components, and elements that will not be described here.

Referring to FIG. 3, electronic device 200 may include, without limitation: a processing architecture 250; a suitable amount of memory 252; device-specific hardware, software, firmware, and applications 254; electronic display 206; a display driver 256; a graphical user interface (GUI) generator 258; and wireless/wired communication module(s) 260. The elements of electronic device 200 may be coupled together via a bus 262 or any suitable interconnection architecture. Those of skill in the art will understand that the various illustrative blocks, modules, circuits, and processing logic described in connection with electronic device 200 may be implemented in hardware, computer software, firmware, or any combination of these. To clearly illustrate this interchangeability and compatibility of hardware, firmware, and software, various illustrative components, blocks, modules, circuits, and processing steps may be described generally in terms of their functionality. Whether such functionality is implemented as hardware, firmware, or software depends upon the particular application and design constraints imposed on the embodiment. Those familiar with the concepts described here may implement such functionality in a suitable manner for each particular application, but such implementation decisions should not be interpreted as causing a departure from the scope of the invention.

Processing architecture 250 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor may be realized as a microprocessor, a controller, a microcontroller, or a state machine. Moreover, a processor may be implemented as a combination of computing devices, e.g., a combination of a digital signal processor and a microprocessor, a plurality of microprocessors, one or more microprocessors in conjunction with a digital signal processor core, or any other such configuration.

Memory 252 may be realized as RAM memory, flash memory, EPROM memory, EEPROM memory, registers, a hard disk, a removable disk, a CD-ROM, or any other form of storage medium known in the art. In this regard, memory 252 can be coupled to processing architecture 250 such that processing architecture 250 can read information from, and write information to, memory 252. In the alternative, memory 252 may be integral to processing architecture 250. As an example, processing architecture 250 and memory 252 may reside in an ASIC.

Device-specific hardware, software, firmware, and applications 254 may vary from one embodiment of electronic device 200 to another. For example, device-specific hardware, software, firmware, and applications 254 will support telephone functions and features when electronic device 200 is realized as a telephone, infusion pump functions and features if electronic device 200 is realized as an infusion pump, and computer functions and features if electronic device 200 is realized as a personal computer. In practice, certain portions or aspects of device-specific hardware, software, firmware, and applications 254 may be implemented in one or more of the other blocks depicted in FIG. 3.

Electronic display 206 is suitably configured to enable electronic device 200 to render and display physiological patient data using a graphical display element, such as intuitive graphical display 202. Of course, electronic display 206 may also be utilized for the display of other information, including, without limitation: status information for devices that communicate with electronic device 200; clock information; alarms; and/or other information and data received or processed by electronic device 200. In practice, electronic display 206 is coupled to display driver 256, which controls and manages the rendering of graphical information on electronic display 206. Notably, the specific configuration, operating characteristics, size, resolution, and functionality of electronic display 206 and display driver 256 can vary depending upon the practical implementation of electronic device 200. For example, if electronic device 200 is a desktop computer, then electronic display 206 may be a CRT, LCD, or plasma monitor. Alternatively, if electronic device 200 is a personal digital assistant, then electronic display 206 may be a small scale integrated LCD, which may include a stylus writing screen, a touchpad, or the like.

GUI generator 258 can be realized as processing logic, and such processing logic may be realized as one or more pieces of software/firmware. For example, GUI generator 258 may be partially or wholly implemented in processing architecture 250, display driver 256, and/or in device-specific hardware, software, firmware, and applications 254. For the embodiments described here, GUI generator 258 may be realized as processing logic configured to dynamically generate graphical elements for display on electronic display 206, including intuitive graphical display 202 of physiological patient data. In this regard, GUI generator 258 produces intuitive graphical display 202 in response to the monitored physiological characteristic data (BG measurement data in this example). To support continuous glucose sensor transmitters, GUI generator 258 is suitably configured to update intuitive graphical display 202 whenever electronic device 200 receives fresh measurement data. In certain embodiments, the graphical elements produced by GUI generator 258 are processed by display driver 256 for rendering on electronic display 206.

An embodiment of electronic device 200 may employ any number of wireless data communication modules and/or any number of wired data communication modules (identified by reference number 260). These data communication modules are suitably configured to support wireless/wired data communication (unidirectional or bidirectional, depending upon the particular implementation) between electronic device 200 and other compatible devices, for example, a continuous sensor transmitter for the monitored physiological characteristic.

A wireless data communication module is configured to support one or more wireless data communication protocols. Any number of suitable wireless data communication protocols, techniques, or methodologies may be supported by electronic device 200, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. In an embodiment of electronic device 200, a wireless data communication module may include or be realized as hardware, software, and/or firmware, such as an RF front end, a suitably configured radio module (which may be a stand alone module or integrated with other or all functions of the device), a wireless transmitter, a wireless receiver, a wireless transceiver, an infrared sensor, an electromagnetic transducer, or the like. Moreover, electronic device 200 may include one or more antenna arrangements (which may be located inside housing 204) that cooperate with the wireless data communication module.

A wired data communication module supports data transfer over a cable, a wired connection, or other physical link. A wired data communication module is configured to support one or more wired/cabled data communication protocols. Any number of suitable data communication protocols, techniques, or methodologies may be supported by electronic device 200, including, without limitation: Ethernet; home network communication protocols; USB; IEEE 1394 (Firewire); hospital network communication protocols; and proprietary data communication protocols. In an embodiment of electronic device 200, a wired data communication module may include or be realized as hardware, software, and/or firmware, such as a suitably configured and formatted port, connector, jack, plug, receptacle, socket, adaptor, or the like.

Figure 4:
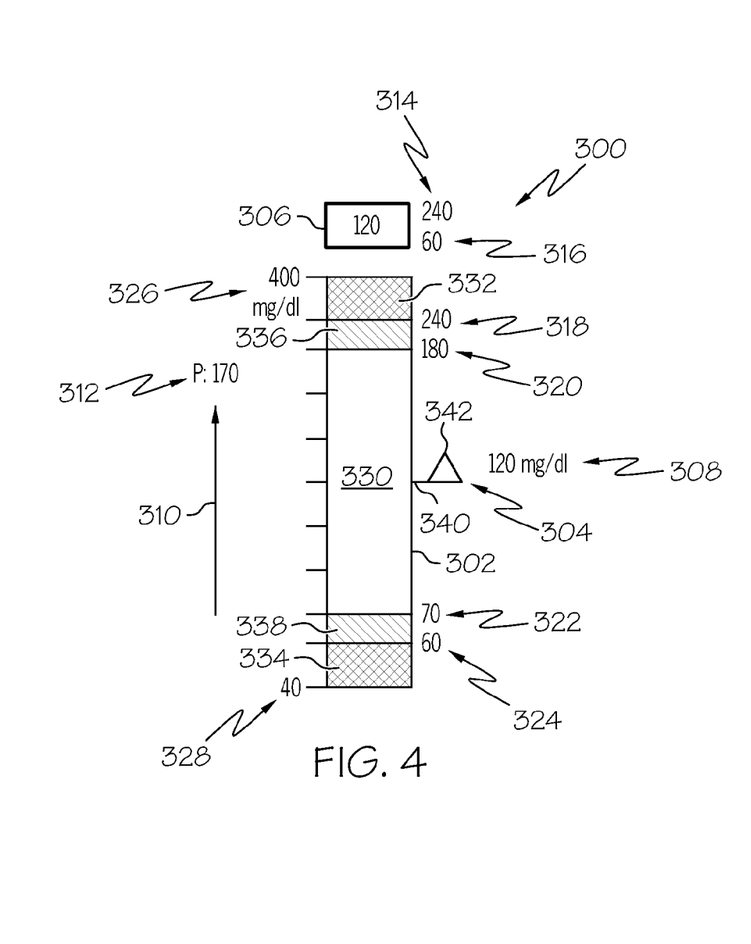
FIGS. 4-7 illustrate a first embodiment of an intuitive graphical display of physiological patient data in different states.
Figure 5:
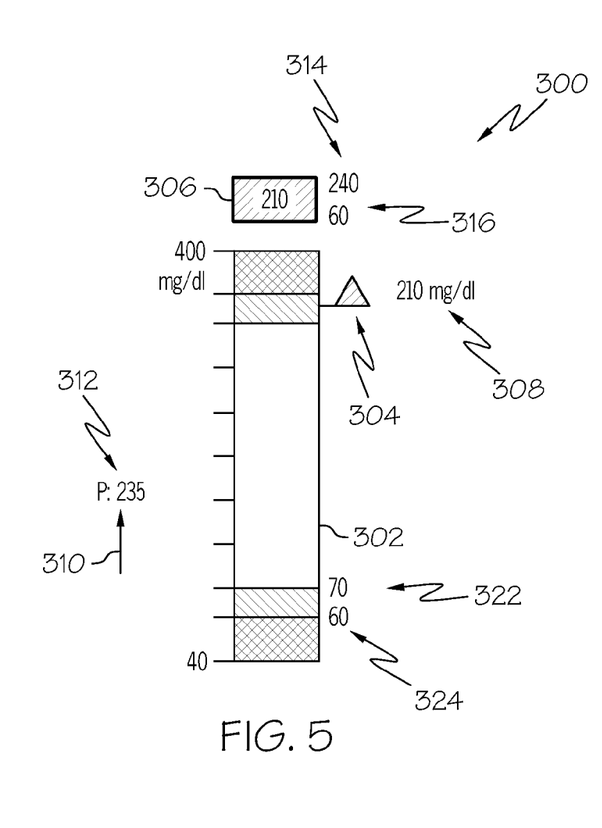
Figure 6:
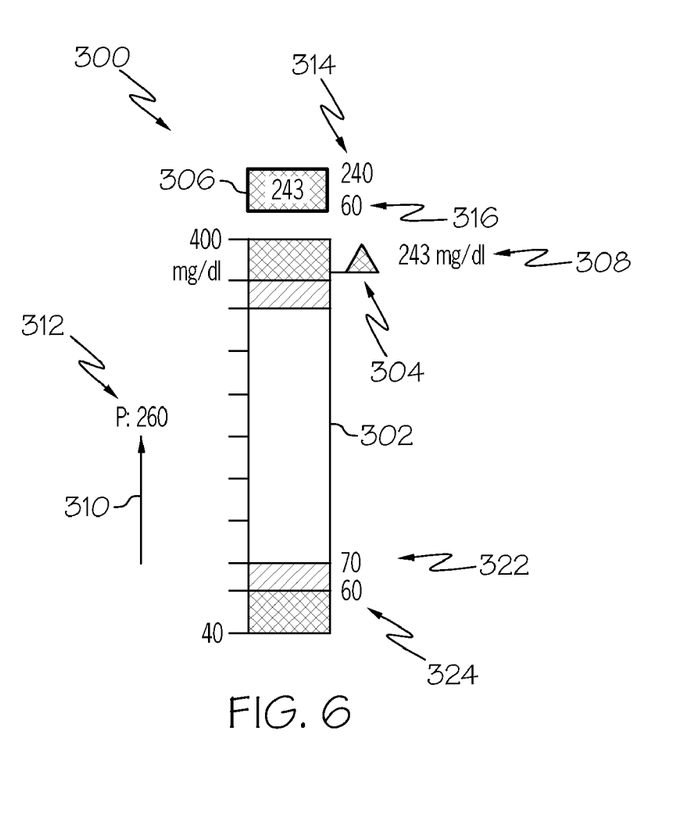
Figure 7:
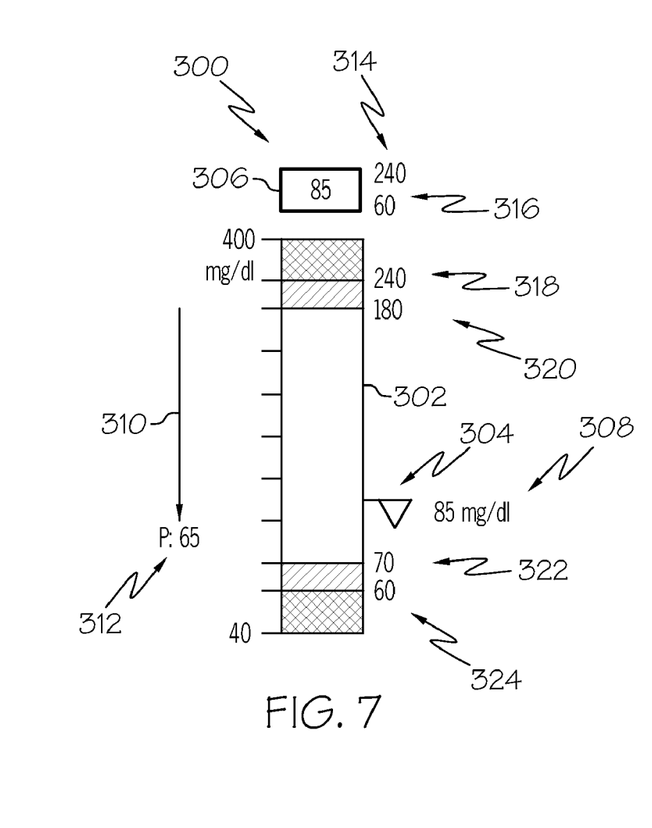

An embodiment of electronic device 200 is suitably configured to render on electronic display 206 a graphical element that represents an intuitive graphical display of physiological patient data (e.g., BG measurement values), regardless of its form factor, native GUI capabilities, display resolution, and graphics rendering capabilities. In this regard, FIGS. 4-7 illustrate a first embodiment of an intuitive graphical display 300 of physiological patient data in different states. The values depicted in the figures represent typical values, and they are not intended to limit or otherwise restrict the embodiments described here. In this regard, typical BG values can range from about 20 mg/dl to over 600 mg/dl. FIG. 4 depicts intuitive graphical display 300 for a normal BG level that is increasing at a relatively high rate of change, FIG. 5 depicts intuitive graphical display 300 for a high BG level that is increasing at a relatively low rate of change, FIG. 6 depicts intuitive graphical display 300 for a very high BG level that is increasing at a relatively intermediate rate of change, and FIG. 7 depicts intuitive graphical display 300 for a normal BG level that is decreasing at a relatively high rate of change. Intuitive graphical display 300 provides the user with a simple graphical presentation of the patient's real time (or near real time) BG value in association with other usable information, such as high/low BG alarm limit ranges, predictive BG values, rate of BG change, and direction of BG change. Intuitive graphical display 300 allows the patient to quickly and easily view, interpret, and assess his or her glucose condition relative to other pertinent data for quick decision making In certain embodiments, intuitive graphical display 300 also provides the user with the capability to access operational device controls for the operation of the host electronic device 200, the corresponding continuous glucose sensor transmitter, and/or other devices that communicate with electronic device 200.

In practice, some or all of the constituent parts of intuitive graphical display 300 can be enabled/disabled by a user to customize the appearance of intuitive graphical display 300. For the sake of completeness, FIGS. 4-7 depict a "full featured" version of intuitive graphical display 300 with all features enabled. Referring to FIG. 4, intuitive graphical display 300 includes, without limitation: a bar graph 302; a measurement value pointer 304; a stationary text field 306 for the current value of the monitored physiological characteristic (e.g., BG level); a moving text field 308 for the current value of the monitored physiological characteristic; a rate of change pointer 310; a text field 312 for a predicted value of the monitored physiological characteristic; a text field 314 for a high alarm limit value; a text field 316 for a low alarm limit value; a text field 318 for a high alarm limit value; a text field 320 for a high early warning limit value; a text field 322 for a low early warning limit value; and a text field 324 for a low alarm limit value. These and other features of intuitive graphical display 300 are described in more detail below.

Bar graph 302, which may be implemented in a vertical orientation as shown or in a horizontal or other orientation, represents the main graphical element in intuitive graphical display 300. Bar graph 302 is preferably calibrated and configured to indicate the desired measurement range for the monitored physiological characteristic. In this example, bar graph 302 has a BG measurement range of 40 mg/dl to 400 mg/dl. The upper and lower range limits may be user configurable to accommodate the patient's condition (e.g., they can be set by accessing an "Options" or "Setup" menu of the host electronic device). The high/low warning and alarm limits may be programmed to change with the time of day or other conditions. For example, the target zone may be increased or the warnings may be eliminated during the night so that the user is only alerted when large excursions occur. As another example, the zones may be changed after meals when the user expects her glucose to increase. The measurement scale may be linear, logarithmic, or non-linear. For example, the target and low ranges may be magnified such that they consume more area of the display (per mg/dl) than the higher range. In practice, the measurement scale range can be selected from a list of pre-defined ranges, the high and low limits can be manually entered, and/or the range can be automatically set based upon historical BG values over a number of sample points and/or over a specified period of time. Thus, intuitive graphical display 300 may also include a text field 326 that alphanumerically indicates the upper measurement range, and a text field 328 that alphanumerically indicates the lower measurement range. Intuitive graphical display 300 may also display the units of measurement, for example, mg/dl or mmol/l, in conjunction with text field 326 (as shown in FIGS. 4-7) and/or in conjunction with text field 328.

Bar graph 302 may include calibration indicia and additional text fields that indicate BG values between the limits of its measurement range. For example, FIG. 4 depicts a plurality of calibrated scale markers on the left side of bar graph 302 (in this embodiment, however, no additional BG values are displayed for the scale markers). Bar graph 302 may also include indicia of the following zones for the monitored physiological characteristic: a target zone 330; a high alarm zone 332; a low alarm zone 334; a high early warning zone 336; and a low early warning zone 338. The host electronic device may allow the user to enable/disable the display of any of these zones (using, for example, an "Options" or "Setup" menu of the host electronic device). Each of these zones is rendered in a manner that makes it easy to distinguish from at least its neighboring zone(s). In practice, the distinguishing indicia may be rendered or realized as any visually distinguishable feature or characteristic, including, without limitation: colors; shading, patterns, or textures; displayed brightness; alphanumeric content; or font characteristics. In certain embodiments of bar graph 302, the zones are color coded in the following manner: target zone 330 is green; high alarm zone 332 and low alarm zone 334 are red; and high early warning zone 336 and low early warning zone 338 are yellow. Of course, alternate color schemes and other distinguishing display characteristics (as mentioned above) may be used.

Notably, the measurement zones of bar graph 302 are calibrated according to the scale of bar graph 302. For example, the upper and lower boundaries of target zone 330 correspond to the appropriate upper and lower BG measurement values on the gradation scale of bar graph 302. Moreover, text field 318 alphanumerically indicates the particular high alarm limit value for the patient's BG, and text field 318 is positioned at or near the boundary line that defines the lower limit of high alarm zone 332. Similarly, text field 320 alphanumerically indicates the particular high early warning limit value for the patient's BG, and text field 320 is positioned at or near the boundary line that defines the lower limit of high early warning zone 336. Likewise, text field 322 alphanumerically indicates the particular low early warning limit value for the patient's BG, and text field 322 is positioned at or near the boundary line that defines the upper limit of low early warning zone 338. In addition, text field 324 alphanumerically indicates the particular low alarm limit value for the patient's BG, and text field 324 is positioned at or near the boundary line that defines the upper limit of low alarm zone 334. For this "full featured" embodiment, text field 314 and text field 318 display the same high alarm limit value, and text field 316 and text field 324 display the same low alarm limit value. Notably, text fields 306, 314, 316, 318, 320, 322, 324, 326, 328 may be displayed in conjunction with bar graph 302.

After the patient-specific settings have been saved, bar graph 302, the displayed zones of bar graph 302, and the various text fields corresponding to the range of bar graph 302 and the upper/lower limits of the displayed zones of bar graph 302 can be displayed in a "static" manner during normal rendering of intuitive graphical display 300. In other words, these features and characteristics need not have dynamically changing or moving characteristics that depend upon the current value of the measured physiological characteristic.

Measurement value pointer 304 represents a dynamic element of intuitive graphical display 300. In this regard, measurement value pointer 304 moves along bar graph 302 to indicate the current value of the monitored physiological characteristic. Accordingly, measurement value pointer 304 may include an arrow, a line, or any suitable marker 340 that is calibrated according to the scale of bar graph 302. For the illustrated embodiment, the vertical position of marker 340 on bar graph 302 indicates the current BG level relative to the corresponding vertical position on the scale of bar graph 302. In FIG. 4, marker 340 corresponds to a BG level of 120 mg/dl. Moreover, text field 308 alphanumerically indicates the current BG value, and text field 308 is positioned at, near, or in combination with measurement value pointer 304. In addition, text field 308 may be dynamically rendered such that it moves along bar graph 302 concurrently with measurement value pointer 304. Intuitive graphical display 300 may also display the units of measurement, for example, mg/dl or mmol/l, in conjunction with text field 308 (as shown in FIGS. 4-7). For this "full featured" embodiment, text field 308 and text field 306 display the same information, i.e., the current value of the monitored physiological characteristic.

Measurement value pointer 304 effectively combines both a real time (or substantially real time) visual identifier of the current BG level and a direction of change indicator within one graphical element. In this regard, measurement value pointer 304 preferably includes a directional pointer 342, which may be coupled to marker 340. Indeed, marker 340 and directional pointer 342 can be rendered together as a combined element. Measurement value pointer 304 (and directional pointer 342 in particular) is suitably configured to indicate a direction of change of the monitored physiological characteristic. Directional pointer 342 is used to indicate whether the patient's BG value is rising or falling. When directional pointer 342 is pointing up (as depicted in FIGS. 4-6), the BG value is on the rise; when directional pointer 342 is pointing down (as depicted in FIG. 7), the BG value is falling.

In certain embodiments, one or more display characteristics of measurement value pointer (in particular, directional pointer 342) change in response to the current value of the monitored physiological characteristic. Any suitable indicia may be rendered or realized as a visually distinguishable feature or characteristic, including, without limitation: colors; shading, patterns, or textures; displayed brightness; or a displayed symbol within directional pointer. For this example, the fill color of directional pointer 342 changes in accordance with the respective zone of bar graph 302 identified by marker 340. Thus, in FIG. 4 and FIG. 7, directional pointer 342 and target zone 330 are both colored green, in FIG. 5, directional pointer 342 and high early warning zone 336 are both colored yellow, and in FIG. 6, directional pointer 342 and high alarm zone 332 are both colored red.

Similarly, one or more display characteristics of text field 306 (which displays the current value of the monitored physiological characteristic) may change in response to the current value of the monitored physiological characteristic. Again, any suitable indicia may be rendered or realized as any visually distinguishable feature or characteristic, including, without limitation: colors; shading, patterns, or textures; displayed brightness; or a displayed symbol within text field 306. For this example, the fill color of text field 306 changes in accordance with the respective zone of bar graph 302 identified by marker 340. Thus, in FIG. 4 and FIG. 7, directional pointer 342, target zone 330, and text field 306 are all colored green, in FIG. 5, directional pointer 342, high early warning zone 336, and text field 306 are all colored yellow, and in FIG. 6, directional pointer 342, high alarm zone 332, and text field 306 are all colored red. Moreover, when measurement value pointer 304 indicates a BG level in high alarm zone 332 or in low alarm zone 334, then the fill color and/or the characters in text field 306 may flash on and off to convey a sense of urgency. Likewise, the characters in text field 318 and/or the characters in text field 314 (i.e., the high alarm limit value itself) may change color or flash on and off when measurement value pointer 304 indicates a BG level in high alarm zone 332, and the characters in text field 324 and/or the characters in text field 316 (i.e., the low alarm limit value itself) may change color or flash on and off when measurement value pointer 304 indicates a BG level in low alarm zone 334. Similar flashing and/or coloring techniques may be utilized when measurement value pointer 304 indicates a BG level in high early warning zone 336 or in low early warning zone 338.

Rate of change pointer 310 is rendered such that it indicates the rate of change of the monitored physiological characteristic. Rate of change pointer 310 can be displayed in any suitable orientation and location; this embodiment renders rate of change pointer 310 in a vertical orientation and to the left of bar graph 302. Here, rate of change pointer 310 is realized as an upward or downward pointing arrow having a variable length, where the displayed length corresponds to the magnitude of the rate of change. Notably, the direction of the arrow also serves to indicate the direction of change of the monitored physiological characteristic: an upward arrow represents an increasing trend, while a downward arrow represents a decreasing trend. In this regard, the direction of rate of change pointer 310 also corresponds to the direction of directional pointer 342.

The length of rate of change pointer 310 may be continuously variable or it may be one of a limited number of predefined lengths. The illustrated embodiment employs a simple approach where the length of rate of change pointer 310 may be short, intermediate, or long (corresponding to a relatively low rate of change, a relatively intermediate rate of change, or a relatively high rate of change, respectively). Here, FIG. 4 depicts a condition where rate of change pointer 310 is a relatively long upward pointing arrow, thus indicating that the BG level is increasing at a relatively high rate. In contrast, FIG. 5 depicts a condition where the rate of change pointer indicates that the BG level is increasing at a relatively low rate, and FIG. 6 depicts a condition where the rate of change pointer indicates that the BG level is increasing at a relatively intermediate rate. On the other hand, FIG. 7 depicts a condition where the rate of change pointer is rendered as a relatively long downward pointing arrow, thus indicating that the BG level is decreasing at a relatively high rate.

Text field 312 is utilized to display a predicted value of the monitored physiological characteristic. The host electronic device may be configured to generate the predicted value as an estimated projection based upon historical and empirical values, historical trends and patterns for the given patient, or the like. The predicted value may represent an extrapolated value that will occur at a predefined time in the future, for example, thirty minutes ahead. The predefined time may be user selectable (e.g., 5-60 minutes). Text field 312 can be displayed in any suitable orientation and location; this embodiment renders text field 312 above or below the arrowhead of rate of change pointer 310. Indeed, text field 312 may be dynamically rendered in combination with rate of change pointer 310 such that it moves up and down concurrently with rate of change pointer 310. To distinguish the predicted value from the current value, text field 312 has the format "P: yyy", where "P" indicates that the displayed value is a predicted value. Intuitive graphical display 300 may also display the units of measurement, for example, mg/dl or mmol/l, in conjunction with text field 312 (this item is not shown in FIGS. 4-7). Alternatively, the rate of change pointer may be combined with the direction pointer, and the length of the direction pointer could extend to the predicted glucose level. For example, in FIG. 4, directional pointer 342 could instead be extended upward such that its apex corresponds to the predicted value of 170 mg/dl. In such an embodiment, it may not be necessary to display rate of change pointer 310 and text field 312.

Intuitive graphical display 300 may also include at least one control button field that, when activated, initiates a control function of the host electronic device. As used here, a "control button field" is a displayed feature that functions as a soft key, an interactive touch screen item, an icon or element that can be selected with a mouse or other GUI pointing mechanism, or the like. A control button field can be displayed in any suitable orientation and location within intuitive graphical display 300, and possibly in conjunction with another displayed feature or element. For example, this particular embodiment utilizes text field 306 as a control button field. In FIG. 4, the control button aspect of text field 306 is indicated with the bolded outline. Of course, a practical implementation may highlight or distinguish text field 306 using any visually distinguishable technique or characteristics.

The control button field can be activated to initiate any control function, feature, or operation of the host electronic device. Moreover, the functionality of the control button field may vary depending upon the current state of intuitive graphical display 300. In particular, the functionality of the control button field may change in accordance with the current BG level. For example, activation of the control button field may launch a different display screen, generate a small sub-window within the existing display screen, pull up a menu, disable an alarm, instruct the host electronic device to transmit a command to another device, etc. The use of such active control button fields is particularly desirable for networked deployments where the host electronic device can communicate with and operate in conjunction with other devices such as an insulin infusion pump, a bedside glucose monitor, or the like.

To briefly summarize, operation of an embodiment of the host electronic device may be as follows. A high early warning condition is enabled at the host electronic device when the current BG value rises above the high early warning value (identified in text field 320). In response to this condition, the fill color of text field 306 changes to yellow. This indicates to the user that the current BG value is near to the high alarm value (identified in text field 318). A high alarm condition is enabled at the host electronic device when the current BG value rises above the high alarm value. In response to this condition, the fill color of text field 306 changes to flashing red. In addition, the characters in text field 314 and/or in text field 318 are displayed in a flashing manner. This indicates to the user that the current BG value has exceeded the high alarm value. A low early warning condition is enabled at the host electronic device when the current BG value falls below the low early warning value (identified in text field 322). In response to this condition, the fill color of text field 306 changes to yellow. This indicates to the user that the current BG value is near to the low alarm value (identified in text field 324). A low alarm condition is enabled at the host electronic device when the current BG value falls below the low alarm value. In response to this condition, the fill color of text field 306 changes to flashing red. In addition, the characters in text field 316 and/or in text field 324 are displayed in a flashing manner. This indicates to the user that the current BG value has fallen below the low alarm value. In practice, the transition from one state to another may be initiated only after the current value has remained in a given measurement zone for at least a threshold time period to avoid false alarm conditions.

The displayed characteristics and/or the number of items of intuitive graphical display 300 may also dynamically change as needed to ensure readability. For example, in FIG. 5 and FIG. 6, intuitive graphical display 300 does not include text field 318 or text field 320, which might otherwise interfere with the display of measurement value pointer 304.

Figure 8:
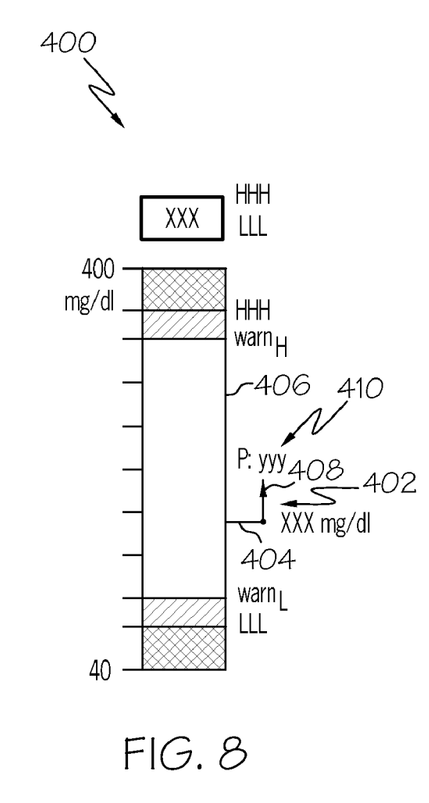
FIGS. 8-10 illustrate a second embodiment of an intuitive graphical display of physiological patient data in different states.
Figure 9:
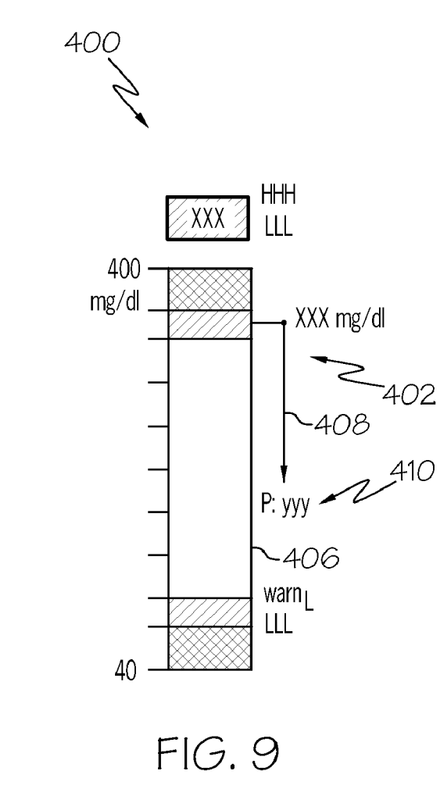
Figure 10:
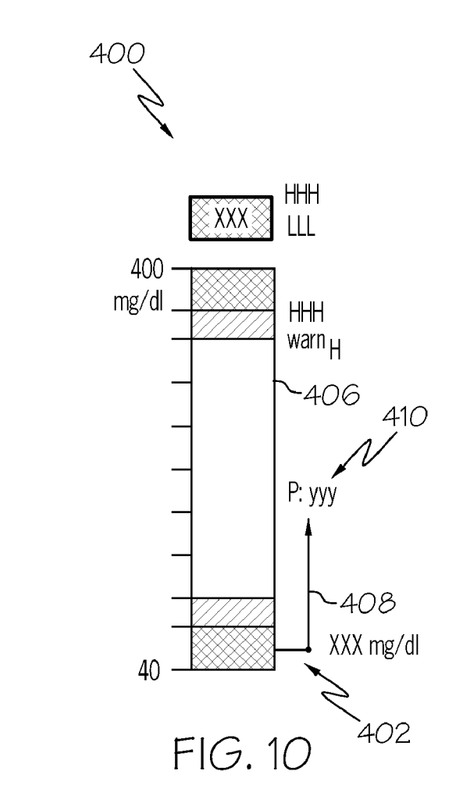

FIGS. 8-10 illustrate a second embodiment of an intuitive graphical display 400 of physiological patient data in different states. Intuitive graphical display 400 includes a number of features and elements that were described above for intuitive graphical display 300. For the sake of brevity, shared features, elements, and aspects will not be redundantly described here in the context of intuitive graphical display 400. FIG. 8 depicts intuitive graphical display 400 for a normal BG level that is increasing at a relatively low rate of change, FIG. 9 depicts intuitive graphical display 400 for a high BG level that is decreasing at a relatively high rate of change, and FIG. 10 depicts intuitive graphical display 400 for a very low BG level that is increasing at a relatively intermediate rate of change.

In contrast to intuitive graphical display 300, which utilizes a separate and distinct rate of change pointer 310, intuitive graphical display 400 integrates a rate of change pointer into its measurement value pointer. Referring to FIG. 8, intuitive graphical display 400 includes a measurement value pointer 402, which has the general characteristics and functionality of measurement value pointer 304 described above. In this regard, measurement value pointer 402 includes a marker 404 that is rendered such that it is calibrated according to the scale of the bar graph 406. Measurement value pointer 402 also incorporates a rate of change pointer 408 that functions in the same manner as rate of change pointer 310 to indicate the rate of change of the monitored physiological characteristic; namely, rate of change pointer 408 has a displayed length that corresponds to the magnitude of the rate of change.

Notably, rate of change pointer 408 also indicates the direction of change of the monitored physiological characteristic. For this example, the direction of the arrowhead of rate of change pointer 408 indicates whether the monitored physiological characteristic is rising or falling. Thus, FIG. 8 depicts a state where the relatively short upward pointing arrow for rate of change pointer 408 corresponds to a BG value that is rising at a relatively low rate, FIG. 9 depicts a state where the relatively long downward pointing arrow for rate of change pointer 408 corresponds to a BG value that is decreasing at a relatively high rate, and FIG. 10 depicts a state where the relatively intermediate length upward arrow for pointing rate of change pointer 408 corresponds to a BG value that is increasing at a relatively moderate rate.

Intuitive graphical display 400 may include a text field 410 that alphanumerically indicates a predicted value of the monitored physiological characteristic. Text field 410 can be displayed in any suitable orientation and location; this embodiment renders text field 410 above or below the arrowhead of rate of change pointer 408. Indeed, text field 410 may be dynamically rendered in combination with rate of change pointer 408 such that it moves along bar graph 406 concurrently with measurement value pointer 402.

Figure 11:
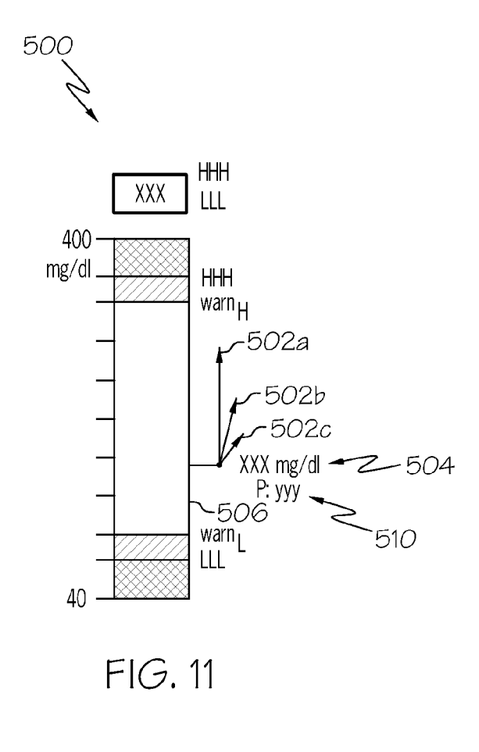
FIGS. 11-13 illustrate a third embodiment of an intuitive graphical display of physiological patient data in different states.
Figure 12:
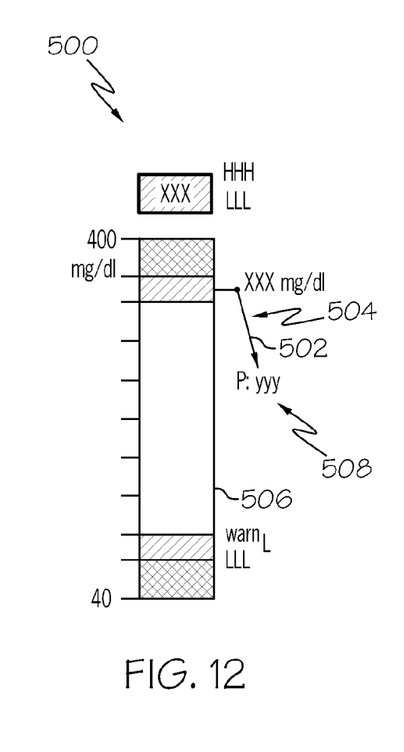
Figure 13:
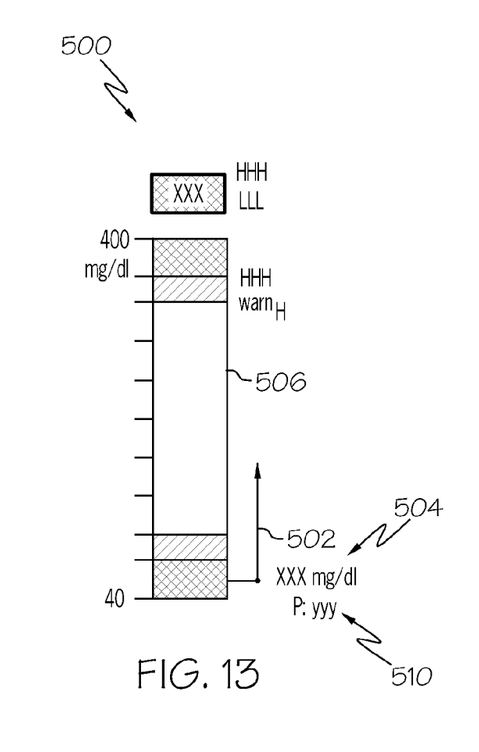

FIGS. 11-13 illustrate a third embodiment of an intuitive graphical display 500 of physiological patient data in different states. Intuitive graphical display 500 includes a number of features and elements that were described above for intuitive graphical display 300 and/or for intuitive graphical display 400. For the sake of brevity, shared features, elements, and aspects will not be redundantly described here in the context of intuitive graphical display 500. FIG. 11 depicts intuitive graphical display 500 for a normal BG level that is increasing, FIG. 12 depicts intuitive graphical display 500 for a high BG level that is decreasing at a relatively moderate rate of change, and FIG. 13 depicts intuitive graphical display 500 for a very low BG level that is increasing at a relatively high rate of change.

Intuitive graphical display 500 is similar to intuitive graphical display 400, however, intuitive graphical display 500 employs a rate of change pointer 502 that is rendered at different angles that represent different rates of change. Rate of change pointer 502 is incorporated into a measurement value pointer 504 for intuitive graphical display 500. Referring to FIG. 11, rate of change pointer 502 has a displayed angle relative to a major axis of the bar graph 506 of intuitive graphical display 500. For the illustrated embodiment, the major axis corresponds to the longitudinal (vertical) axis of bar graph 506, which also corresponds to the rightmost edge of bar graph. The angle of rate of change pointer 502 corresponds to the magnitude of the rate of change of the monitored physiological characteristic. In practice, the angle formed by rate of change pointer 502 may be continuously variable or it may be one of a limited number of predefined angles. This particular embodiment employs a simple approach where the angle associated with rate of change pointer 502 may be one of three predefined and distinguishable angles (a relatively low angle, such as zero degrees; a relatively intermediate angle, such as twenty degrees; and a relatively high angle, such as forty degrees).

In certain embodiments, the displayed angle of rate of change pointer 502 is relatively low for a relatively high rate of change, and the displayed angle is relatively high for a relatively low rate of change. For example, in FIG. 11, rate of change pointer 502a, which forms a low angle with bar graph 506, corresponds to a relatively high rate of change, rate of change pointer 502b, which forms an intermediate angle with bar graph 506, corresponds to a relatively moderate rate of change, and rate of change pointer 502c, which forms a high angle with bar graph 506, corresponds to a relatively low rate of change. FIG. 11 is used here to illustrate different possible angles for rate of change pointer 502; during normal operation, only one rate of change pointer 502 is rendered at any given time. For the illustrated embodiment, the length of rate of change pointer 502 also changes to indicate the rate of change of the physiological characteristic (as described above for rate of change pointer 408).

FIG. 12 depicts a condition where rate of change pointer 502 is an intermediate length downward pointing arrow that forms a relatively intermediate angle with bar graph 506. This indicates that the BG level is decreasing at a relatively moderate rate. In contrast, FIG. 13 depicts a condition where rate of change pointer 502 is a long upward pointing arrow that forms a relatively low angle (e.g., zero degrees) with bar graph 506. This indicates that the BG level is increasing at a relatively high rate.

Intuitive graphical display 500 may include a text field 508 (FIG. 12) that alphanumerically indicates a predicted value of the monitored physiological characteristic, as described above for text field 410 in the context of intuitive graphical display 400. Alternatively, intuitive graphical display 500 (and any of the other embodiments described herein) may utilize an equivalent text field 510 that is instead rendered near the base of rate of change pointer 502 (FIG. 11 and FIG. 13).

Figure 14:
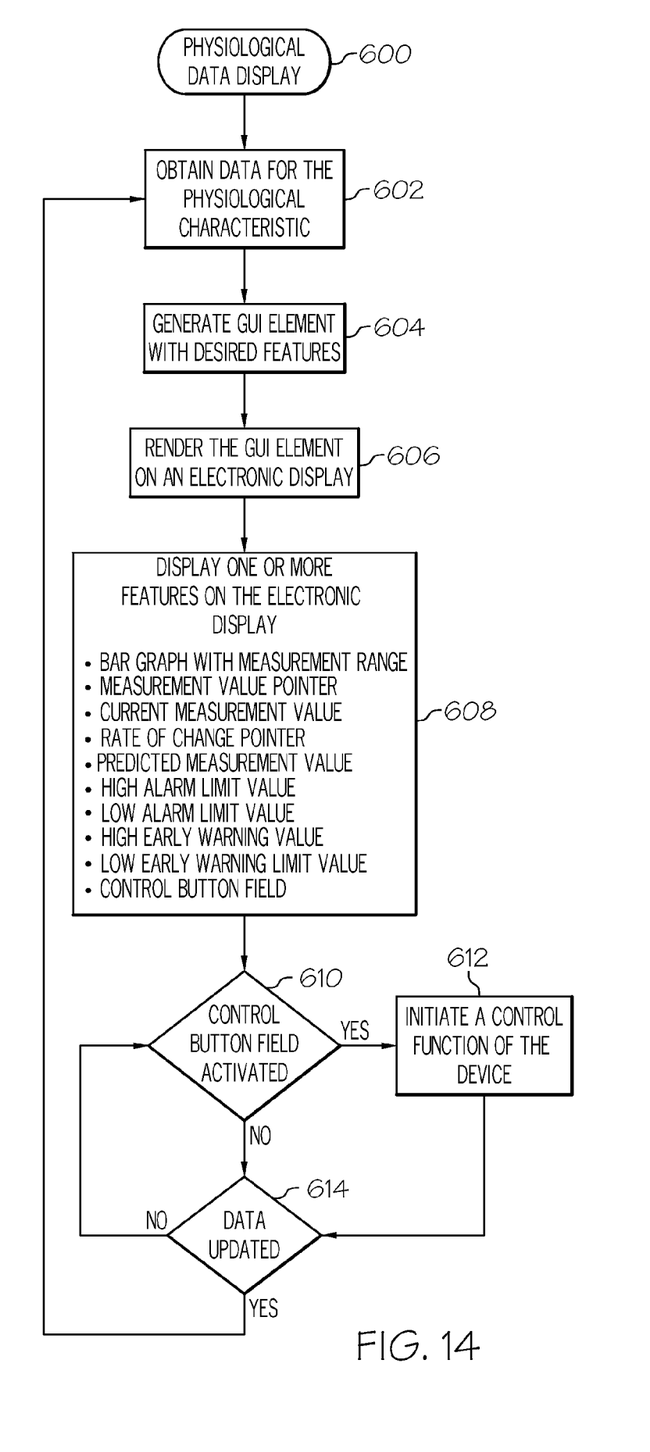
FIG. 14 is a flow chart of an embodiment of a physiological data display process.

FIG. 14 is a flow chart of an embodiment of a physiological data display process 600, which may be performed by a host electronic device to process, generate, and render an intuitive graphical display having the characteristics described above. The various tasks performed in connection with process 600 may be performed by software, hardware, firmware, or any combination thereof. For illustrative purposes, the following description of process 600 may refer to elements mentioned above in connection with FIGS. 1-13. In practice, portions of process 600 may be performed by different elements of the described system, e.g., GUI generator 258, display driver 256, or electronic display 206 (FIG. 3). It should be appreciated that process 600 may include any number of additional or alternative tasks, the tasks shown in FIG. 14 need not be performed in the illustrated order, and process 600 may be incorporated into a more comprehensive procedure or process having additional functionality not described in detail herein.

Process 600 may begin by obtaining data corresponding to a monitored physiological characteristic (task 602), such as the BG level of a patient. In response to the obtained data, process 600 generates, for display on the host electronic device, a graphical element (e.g., a GUI element such as any of the intuitive graphical displays described herein) having the desired features, display characteristics, and functionality (task 604). These features, characteristics, and functionality were described above in detail. The generated graphical element may then be rendered (task 606) for displaying on the electronic display. In connection with such rendering, process 600 will display one or more graphical features, items, and components on the electronic display (task 608). For example, task 608 may display on the electronic display any of the following features, individually or in any desired combination: a bar graph with a measurement range for the monitored physiological characteristic; a measurement value pointer; the current measurement value; a rate of change pointer; a predicted measurement value; a high alarm limit value; a low alarm limit value; a high early warning limit value; a low early warning limit value; a control button field; any additional feature described herein; and possibly other features.

If a displayed control button field is activated (query task 610) by the user of the host electronic device, then process 600 may initiate an appropriate control function of the host electronic device. In practice, a user of the host electronic device can activate a control button field using, for example, a touch screen upon which the control button field is rendered, a touchpad, a mouse, a keyboard or a keypad in conjunction with a displayed soft key feature, or the like. After initiation of this control function, or if a control button field is not activated, then process 600 may check whether the physiological patient data has been updated (query task 614). If the physiological data has not been updated, then process 600 may be re-entered at, for example query task 610. In other words, process 600 may idle until a control button field is activated or the patient data is updated. When the patient data is updated (query task 614), process 600 may be re-entered at, for example, task 602. This enables process 600 to obtain the updated physiological characteristic data and, in response thereto, update the intuitive graphical display rendered on the host device. In this manner, the intuitive graphical display can be continuously (or periodically) refreshed during normal operation of the host device to provide a real time (or near real time) visual display of the monitored physiological characteristic.

While at least one example embodiment has been presented in the foregoing detailed description, it should be appreciated that a vast number of variations exist. It should also be appreciated that the example embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An electronic device having rendered thereon an intuitive graphical display of physiological patient data, comprising:
    a calibrated bar graph that indicates a measurement range for a monitored physiological characteristic; and
    a measurement value pointer that moves along the calibrated bar graph to indicate a current value of the monitored physiological characteristic and a direction of change of the monitored physiological characteristic, the measurement value pointer comprising a marker extending from the calibrated bar graph and rendered such that its position is calibrated according to the scale of the calibrated bar graph, and the measurement value pointer further comprising a rate of change pointer integrated with the marker to indicate the direction of change of the monitored physiological characteristic, the rate of change pointer having a base located at the marker, the rate of change pointer terminating at an apex extending from the base, and the rate of change pointer having a displayed length that corresponds to the magnitude of the rate of change of the monitored physiological characteristic, and wherein the displayed length of the rate of change pointer is variable such that the apex is positioned relative to the scale of the calibrated bar graph to indicate a predicted value of the monitored physiological characteristic.

2. The electronic device of claim 1, wherein the intuitive graphical display of physiological patient data further comprises a text field that alphanumerically indicates the current value of the monitored physiological characteristic, and wherein the text field moves along the calibrated bar graph concurrently with the measurement value pointer.

3. The electronic device of claim 1, wherein display characteristics of the measurement value pointer change in response to the current value of the monitored physiological characteristic.

4. The electronic device of claim 1, wherein the intuitive graphical display of physiological patient data further comprises a text field that alphanumerically indicates a predicted value of the monitored physiological characteristic.

5. The electronic device of claim 4, wherein the text field moves along the calibrated bar graph concurrently with the measurement value pointer.

6. In an electronic device having an electronic display, a method of providing an intuitive graphical display of physiological patient data, the method comprising:
  obtaining data corresponding to a monitored physiological characteristic;
  generating, for display on the electronic display, a graphical element comprising a calibrated bar graph that indicates a measurement range for the monitored physiological characteristic, and a measurement value pointer that moves along the calibrated bar graph to indicate a current value of the monitored physiological characteristic and a direction of change of the monitored physiological characteristic, the measurement value pointer comprising a marker extending from the calibrated bar graph and rendered such that its position is calibrated according to the scale of the calibrated bar graph, and the measurement value pointer further comprising a rate of change pointer integrated with the marker to indicate the direction of change of the monitored physiological characteristic, the rate of change pointer having a base located at the marker, the rate of change pointer terminating at an apex extending from the base, and the rate of change pointer having a displayed length that corresponds to the magnitude of the rate of change of the monitored physiological characteristic, and wherein the displayed length of the rate of change pointer is variable such that the apex is positioned relative to the scale of the calibrated bar graph to indicate a predicted value of the monitored physiological characteristic; and
  rendering the graphical element on the electronic display.

7. The method of claim 6, wherein the graphical element further comprises a text field that alphanumerically indicates a predicted value of the monitored physiological characteristic, the text field rendered above or below the apex of the rate of change pointer such that the text field moves in accordance with movement of the measurement value pointer and in accordance with the displayed length of the rate of change pointer.

8. The method of claim 6, wherein the electronic device is a device selected from the group consisting of: a patient-wearable monitor; a patient-wearable fluid infusion pump; a remote display monitor; a patient monitor; a measurement device for the monitored physiological characteristic; a wireless telephone; a computing device; a television; a personal digital assistant; a digital media player; and a portable video game device.

9. A method for displaying, on an electronic display of a device, an intuitive graphical display of physiological patient data, the method comprising:
  obtaining, at the device, data corresponding to a monitored physiological characteristic;
  displaying, on the electronic display, a bar graph having a calibrated scale that indicates a measurement range for the monitored physiological characteristic; and
  displaying, on the electronic display, a measurement value pointer that indicates a current value of the monitored physiological characteristic on the bar graph, and that indicates a direction of change of the monitored physiological characteristic;
  wherein the measurement value pointer comprises a marker extending from the bar graph and rendered such that the position of the marker is calibrated according to the calibrated scale of the bar graph, and comprises a rate of change pointer integrated with the marker to indicate the direction of change of the monitored physiological characteristic, the rate of change pointer having a base located at the marker and terminating at an apex extending from the base;
  wherein the rate of change pointer has a displayed length that corresponds to the magnitude of the rate of change of the monitored physiological characteristic, the displayed length being variable such that the apex is positioned relative to the scale of the bar graph to indicate a predicted value of the monitored physiological characteristic; and
  wherein the rate of change pointer has a displayed angle, relative to a major longitudinal axis of the bar graph, that also corresponds to the magnitude of the rate of change of the monitored physiological characteristic.

10. The method of claim 9, further comprising displaying, on the electronic display and in conjunction with the bar graph and the measurement value pointer, a text field that alphanumerically indicates a predicted value of the monitored physiological characteristic.

11. The method of claim 10, wherein the text field is rendered above or below the apex of the rate of change pointer such that the text field moves in accordance with movement of the measurement value pointer, in accordance with the displayed length of the rate of change pointer, and in accordance with the displayed angle of the rate of change pointer.

* * * * *